United States Patent [19]

Maryanoff et al.

[11] 4,421,917
[45] Dec. 20, 1983

[54] DERIVATIVES OF 2-UREIDO-7-PHENYLHEXAHYDROBENZO[a]QUINOLIZINES

[75] Inventors: Bruce E. Maryanoff, New Hope; David F. McComsey, Warminster, both of Pa.

[73] Assignee: McNeilab, Inc., Fort Washington, Pa.

[21] Appl. No.: 399,029

[22] Filed: Jul. 16, 1982

[51] Int. Cl.³ .............................................. C07D 455/06
[52] U.S. Cl. ...................................... 546/95; 424/258; 546/144
[58] Field of Search ........................................ 546/95

[56] References Cited

U.S. PATENT DOCUMENTS 3,634,431  1/1972  Van Dyke .............................. 546/95
4,076,820  2/1978  Archibald et al. ................ 546/95 X

FOREIGN PATENT DOCUMENTS 1098569  1/1968  United Kingdom ................... 546/95

Primary Examiner—Richard A. Schwartz

[57] ABSTRACT

2-Ureido-7-phenylhexahydrobenzo[a]quinolizines of the structural formula,

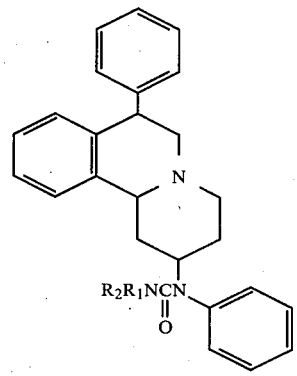

(I)

wherein $R_1 = H$ or lower alkyl (one to three carbons) and $R_2 = H$, lower alkyl (one to six carbons), or phenyl, and which exhibit antihypertensive activity.

5 Claims, No Drawings

DERIVATIVES OF 2-UREIDO-7-PHENYLHEXAHYDROBENZO[A]-QUINOLIZINES

This invention relates to novel compounds, which are urea derivatives of 2-anilino-7-phenylhexahydrobenzo[a]quinolizines. More particularly, the invention is concerned with compounds represented by the following formula (I),

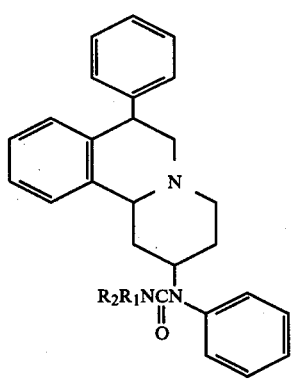

(I)

acid addition salts thereof, novel processes for the preparation of such compounds, and novel intermediates for the preparation of such compounds, wherein $R_1$ is H or a $C_{1-3}$ lower alkyl and $R_2$ is H or a $C_{1-6}$ lower alkyl or phenyl.

In the carbamyl group $C(O)NR_1R_2$ in the above formula (I) when $R_1$ is a $C_{1-3}$ lower alkyl it can be straight or branched chain e.g., methyl, ethyl, propyl or isopropyl, and when $R_2$ is a $C_{1-6}$ lower alkyl it can be straight or branched chain e.g., methyl, ethyl, propyl, isopropyl, butyl, t-butyl, pentyl, hexyl, etc.

Each formula I compound describes and comprises four diastereomeric substances, themselves pairs of enantiomers. The diastereomers, isolated in their pure form, may differ in biological activity, but each has some antihypertensive activity and some have other pharmacological activities as well.

The various diastereomers of each formula I compound are distinguished herein using the nomenclature recommended by Chemical Abstracts for representing the relative configuration of diastereomers of fused-ring compounds ($\alpha/\beta$ nomenclature). Thus, the following designations are employed:

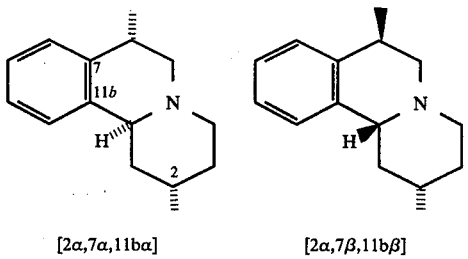

[2α,7α,11bα]    [2α,7β,11bβ]

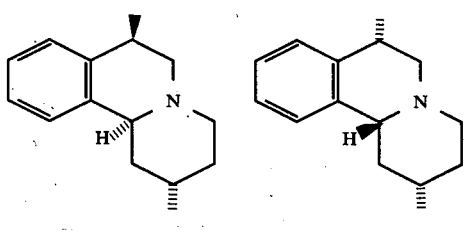

[2α,7β,11bα]    [2α,7α,11bβ]

The compounds of this invention may be prepared according to the following reaction sequences:

(A) Ketone Intermediate:

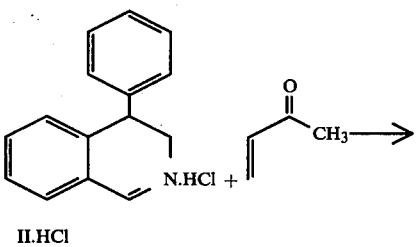

II.HCl

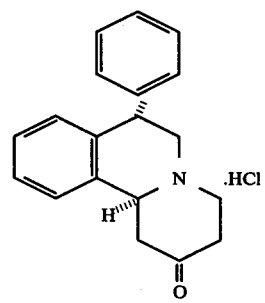

III.HCl (B) Aniline Intermediates:

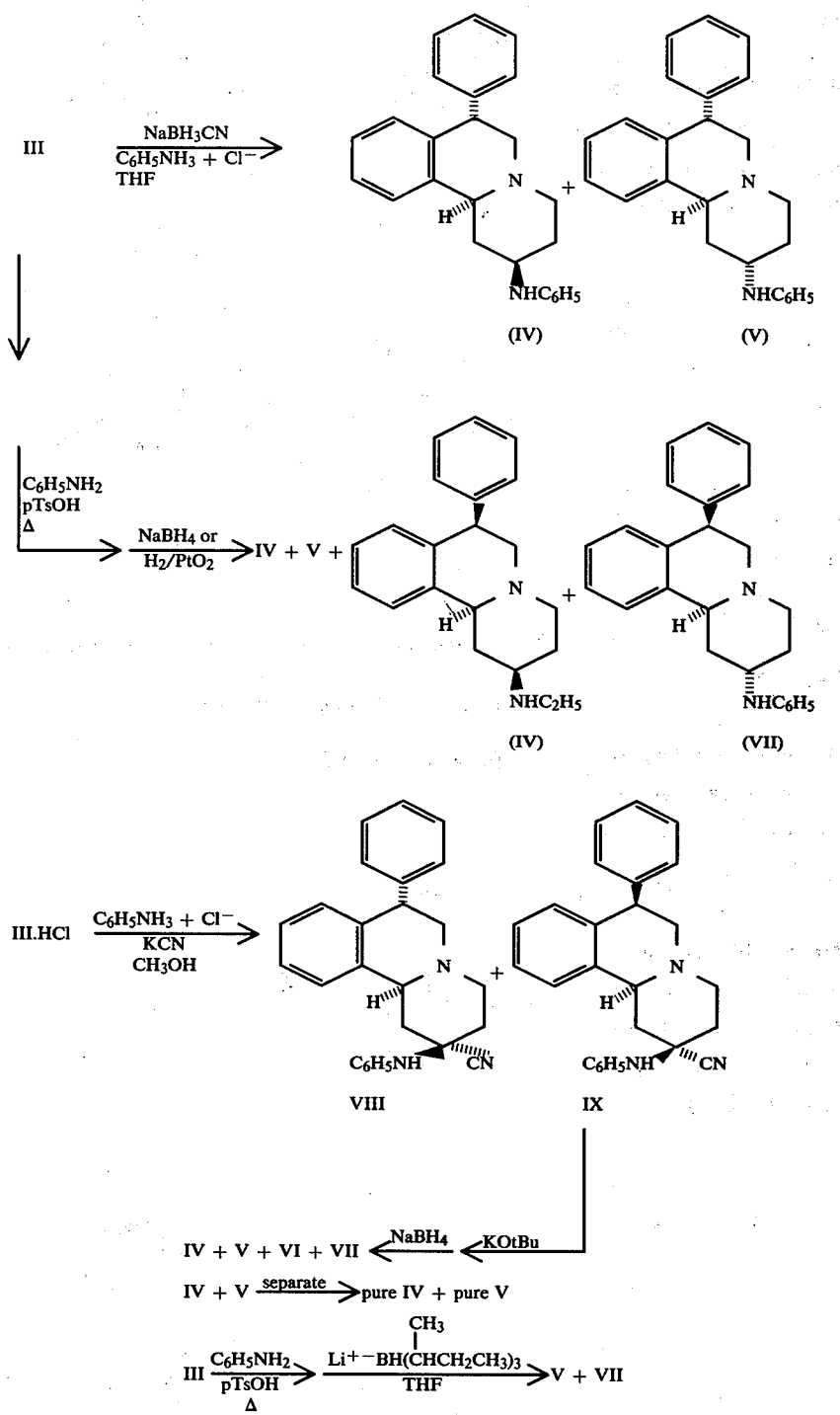
(C) Urea Products:
General

-continued
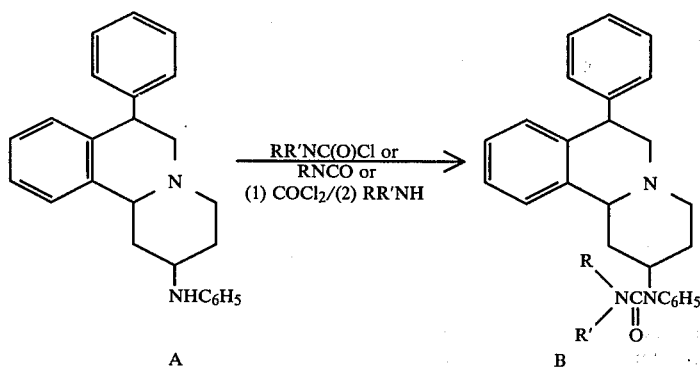
Specific
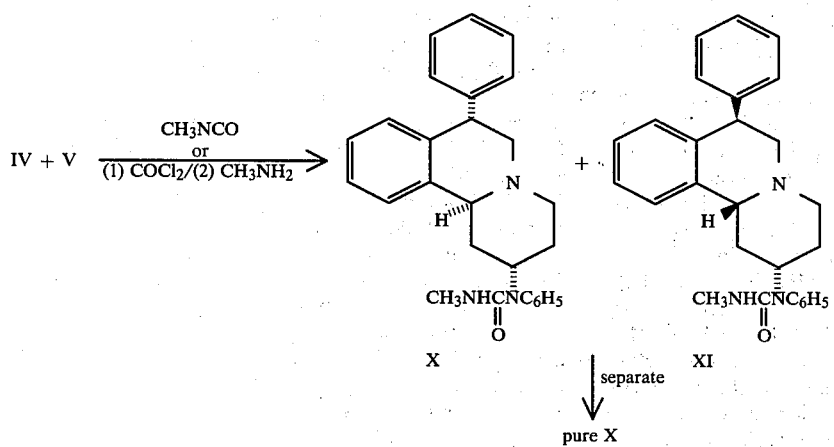
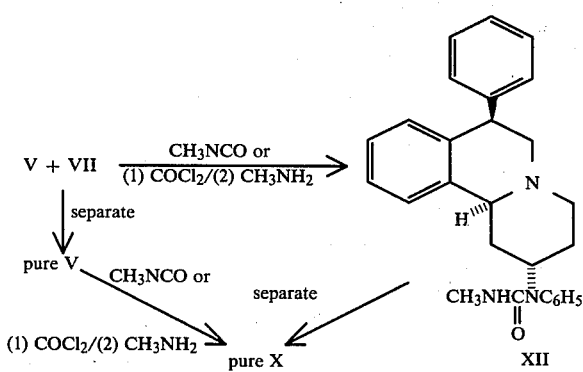
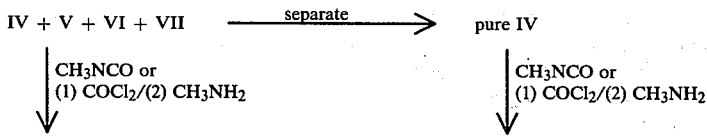

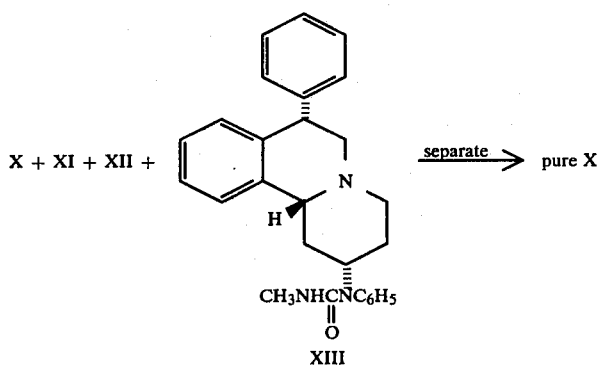

X + XI + XII + → (separate) → pure X

XIII

In the reaction sequences, [7α,11bα]-2-oxo-7-phenyl-1,3,4,6,7,11b-hexahydro-2H-benzo[a]quinolizine (III) is reacted with aniline in a suitable solvent with a suitable catalyst to form an imine. The solvent utilized may be toluene, benzene, xylene, and the like. The reaction is heated under reflux in the presence of a catalyst with removal of water by distillation/reflux into a water separator (e.g., a Dean-Stark apparatus). The reaction may be complete in one to twenty-four hours, during which time the theoretical quantity of water will be collected. The catalyst may be an acid catalyst and is advantageously an organic acid such as para-toleuenesulfonic acid (p-TsOH).

The imine that is formed is then reduced to an amine. The reduction may be carried out with NaBH4 or NaBH3CN in a solvent such as methanol, ethanol, or 2-propanol, forming a mixture of four diastereomeric anilines (1,3,4,6,7,11b-hexahydro-N,7-diphenyl 2H-benzo-[a]quinolizin-2-amines; IV-VII). The reduction may also be carried out by catalytic hydrogenation in a suitable solvent (methanol, ethanol, THF, and the like), preferably using PtO2 as a catalyst, forming a mixture of four diastereomeric anilines (IV, V, VI, and VII). The reduction may be performed with lithium tri-sec-butylborohydride (XIV) in an aprotic solvent such as tetrahydrofuran (THF), methylene chloride, ether, etc., forming a mixture of only two diastereomeric anilines (V and VII), whose configurations are designated [2α,7α,11bα] and [2α,7β,11bα].

The amine (aniline) may also be prepared in one step by reductive-amination. That is, reaction of III with NaBH3CN and aniline hydrochloride in a suitable solvent furnishes product anilines. The solvent may be a lower alkanol such as methanol, ethanol; ethers such as tetrahydrofuran (THF), diethylether; chlorinated hydrocarbons such as methylene chloride; and the like, and mixtures of the same. With alcoholic solvents present, four diastereomeric anilines are produced. Advantageously, the reductive-amination reaction may be conducted with anhydrous THF as a solvent, whereby only two diastereomeric anilines (IV and V), designated [2α,7α,11bα] and [2α,7β,11bβ], are formed.

A mixture of the two diastereomeric imines may be obtained by reaction of ketone III hydrochloride with aniline and alkali metal cyanide in methanol, and reaction of the intermediate anilino nitriles (VIII and IX; [2α,7β,11bβ]- and [2α,7α,11bβ]-2 anilino-7-phenyl-1,3,4,6,7,11b-hexahydro-2H-benzo[a]quinolizine 2-carbonitrile, respectively) with a strong base, such as potassium tert-butoxide, in an inert solvent, such as THF. Reduction of the imines with NaBH4 produces four diastereomeric anilines (IV, V, VI, and VII) and with the sec-butylborohydride (XIV) produces two diastereomeric anilines (V and VII).

The anilines may be purified according to standard techniques known by one skilled in the art (e.g., recrystallization or liquid chromatography). The aniline (A) is reacted with a carbamyl halide or with an isocyanate, or with phosgene followed by an amine (such as ammonia, an alkylamine, or a dialkylamine) to form the urea (B) in an inert solvent (THF, methylene chloride, toluene, and the like). The reaction may be conducted between −20° and 110°, depending on the reaction rate and choice of solvent. The resulting urea may be purified according to standard practices. By this means, the various N-(1,3,4,6,7,11b-hexahydro-7-phenyl-2H-benzo[a]quinolizin-2-yl)-N'-methyl-N-phenylurea compounds (X, XI, XII, XIII) are prepared, employing methyl isocyanate, or phosgene followed by methylamine.

The ketone starting material in the reaction sequence, 2-oxo-7-phenyl-1,3,4,6,7,11b-hexahydro-2H-benzo[a]quinolizine (III), may be prepared by heating 4-phenyl-3,4-dihydroisoquinoline hydrochloride (II.HCl) with excess methylvinylketone according to the experimental description of Unger and coworkers (U.S. Pat. No. 3,553,218 and U.S. Pat. No. 3,393,198).

Separation of diastereomers may be effected at either the aniline or urea stage. Separation procedures well-known to those skilled in the art of organic chemistry such as fractional crystallization or liquid chromatography of free bases, or fractional crystallization of acid addition salts, are suitable.

Anilines IV and VI, and V and VII, may be interconverted by treatment with base. More specifically, heating of IV, V, VI or VII in aqueous dimethylsulfoxide around 100°-150° in the presence of an alkali metal hydroxide (such as NaOH or KOH) for 1-6 hours, or in the presence of an alkali metal carbonate (such as Na2CO3 or K2CO3) for several days, gives rise to mixtures IV/VI, V/VII, VI/IV, or VII/V, respectively, with nearly equivalent quantities of the two isomers in each mixture. By such a process, VI and VII may serve as intermediates to IV and V. These anilines can serve as precursors to the ureas, as noted above. The alkali metal carbonate procedure can also be used to produce ureas X and XI from ureas XII and XIII.

Compounds of the invention may be prepared and utilized in the form of the free base. The compounds may also be used as pharmacologically-acceptable, nontoxic addition salts of inorganic or organic acids such as halogen acids, sulfuric acid, maleic acid, hexamic acid, and the like.

Compounds of this invention are endowed with useful biological activity in the cardiovascular system. In particular the claimed compounds lower blood pressure in warm-blooded animals, and thus are useful as antihypertensive agents. The utility of the compounds is based on a standard test for antihypertensive agents in rats, which possess normally elevated blood pressure. This test entails:

Rodent Antihypertensive Screen

This test evaluates compounds for effects on arterial pressure and heart rate. In this test, the arterial pressure of adult spontaneously hypertensive rats [SHR] (Charles River) is monitored directly via an aortic cannula. The SHR rats are anesthetized with an inhalation anesthetic (methoxyflurane). The left carotid artery is isolated and cannulated. The tip of the cannula is advanced to the aorta and the cannula is exteriorized behind the neck at the level of the scapula. Animals are placed in individual cages and allowed to recover from the anesthetic and are kept unrestrained. The arterial cannula is connected to the pressure transducer which is attached to the recorder. Heart rate is determined from the arterial pressure recording. The test compounds are administered either orally (p.o.) by gavage or by intraperitoneal (i.p.) injection. The arterial pressure and heart rate are monitored for a minimum of 24 hours. A test compound is considered to be active as an antihypertensive agent if the mean arterial pressure (MAP) indicates a fall of >15 mm of Hg. Each animal serves as his own control.

The activity exhibited by the compounds of this invention may be understood by some representative, non-limiting examples.

TABLE I

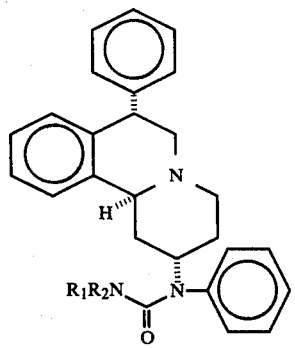

X R$_1$ = H; R$_2$ = CH$_3$
XIV R$_1$ = H; R$_2$ = C$_6$H$_5$
XV R$_1$ = R$_2$ = CH$_3$

| Compound | HX | Δ MAP (mm Hg) at 30 mg/kg, i.p. | Δ MAP (mg/Hg) at 100 mg/kg, p.o. |
|---|---|---|---|
| X | HClO$_4$ | — | −34 |
| XI | HClO$_4$ | −61 | — |
| XIV | — | −19 | — |
| XV | HCl | −46 | −51 |

Ureas, X, XIV, XV, XI showed antihypertensive activity in this test.

The invention will be further understood by referring to the following examples which illustrate the preparation of compounds according to the invention. These examples are given for the purpose of illustration and are not to be construed as limiting the invention in spirit or scope.

EXAMPLE I

[2α,7β,11bβ]- and [2α,7α,11bα]-1,3,4,6,7,11b-Hexahydro-N,7-diphenyl-2H-benzo[a]quinolizin-2-amine (IV and V)

56.5 g (204 mmol) of [7α,11bα]-1,3,4,6,7,11b-hexahydro-7-phenyl-2H-benzo[a]quinolizine-2-one and 45 g of molecular sieves (4A) are combined in 750 ml of dry tetrahydrofuran. 26.5 g (204 mmol) of aniline hydrochloride is added and the mixture is stirred at room temperature for 20 minutes. The reaction is cooled to 2° C. with an ice bath and 12.8 g (204 mmol) of NaCNBH$_3$ is added portionwise over 10 minutes. The reaction is stirred for 45 minutes with continued ice bath cooling. 500 ml of water is added to the reaction and it is stirred for 30 minutes. Then 50 ml of 10 percent NaOH is added and stirring is continued for an additional 30 minutes. This aqueous solution is then extracted with 1500 ml of diethyl ether. The ether solution is washed once with saturated NaCl solution, dried over K$_2$CO$_3$, filtered, and evaporated in vacuo to give about 60 g of oily product. The crude product mixture is dissolved in 100 ml of 2-propanol, heated on a steambath, and treated with 30.4 of cyclohexylsulfamic acid. A solid begins to crystallize immediately while the solution is still hot. The mixture is cooled to room temperature and the white solid is filtered to give [2α,7α,11bα]-1,3,4,6,7,11b-hexahydro-N,7-diphenyl-2H-benzo[a]-quinolizin-2-amine (V) monocyclohexylaminosulfonate. Recrystallization of this solid from methanol gives analytically pure white solid, m.p. 201°–203.5° C. The filtrate from the initial salt formation is evaporated in vacuo to an oil which is partitioned between 1 N NaOH and methylene chloride. The organic phase is washed once with water, once with saturated NaCl solution, and dried over K$_2$CO$_3$. The solution is filtered and evaporated in vacuo to give an oil, which is dissolved in diethyl ether and treated with HCl gas to pH=1. The white HCl salt so formed is filtered to give crude product. The crude salt is stirred with 200 ml of boiling methanol for 10 minutes and filtered. The solid is recrystallized twice from methanol/water (5%) to give analytically pure [2β,7α,11bα]-1,3,4,6,7,11b-hexahydro-N,7-diphenyl-2H-benzo[a]quinolizin-2-amine (IV) dihydrochloride, m.p. 275°–285° C., which contains only ca. 5 percent of V by glc analysis.

EXAMPLE II

N-[2α,7α,11bα]- and [2α,7β,11bβ]-(1,3,4,6,7,11b-Hexahydro-7-phenyl-2H-benzo[a]quinolizin-2-yl)-N′-methyl-N-phenylurea (X and XI)

8.65 g (31 mmol) of [7α,11bα]-1,3,4,6,7,11b-hexahydro-7-phenyl-2H-benzo[a]quinolizine-2-one (III) is dissolved in 125 ml of dry tetrahydrofuran and 6.25 g of molecular sieves (4A) are added. 4.4 g (34 mmol) of aniline hydrochloride is added and the reaction is stirred for 1.5 hours at room temperature. The solution is then cooled to 0° C. and, with stirring, 2.0 g (32 mmol) of NaCNBH$_3$ is added slowly. The solution is stirred at 0° C. for 30 minutes, then added 30 ml of 3 N NaOH solution and 100 ml of ether.

The layers were separated and the organic phase was rinsed with water, dried over Na$_2$SO$_4$, filtered, and evaporated in vacuo to give a viscous oil containing anilines IV and V. Some excess aniline is removed under high vacuum to give about 11 g of a glass, which is dissolved in 50 ml of dry CH₂Cl₂, treated with 2.23 g of CH₃NCO, and stirred overnight (stoppered) at 25° C. The solvent is evaporated and the residue is treated with 50 ml of hot ethylacetate. On cooling and white solid separates, which is predominantly Urea XI. Dissolution in methanol and treatment with 70% HClO₄ gives a white solid. Recrystallization from methanol/ethyl acetate (3:1) affords white needles of XI.HClO₄, mp 247°–250° C. The original ethyl acetate solution, from which XI separated, is evaporated and the residue is dissolved in methanol/ether (1:2). Ethereal HCl is added to convert the base to salt. The white solid that separates is discarded and the solution is treated with NaOH solution. The ether phase is diluted with 1/4 volume of methanol and treated with 70% HClO₄. The solid is mixed with hot methanol and filtered to give X.HClO₄ as a white powder, mp 242°, dec.

EXAMPLE III

N-[2α,7β,11bβ]-(1,3,4,6,7,11b-Hexahydro-7-phenyl-2H-benzo[a]quinolizin-2-yl)-N,N'-diphenylurea 3.5 g (10 mmol) of [2α,7β,11bβ]-1,3,4,6,7,11b-hexahydro-N,7-diphenyl-2H-benzo[a]-quinolizin-2-amine (IV) is combined with 1.31 g (11 mmol) of phenyl isocyanate in 20 ml of dry methylene chloride and is stirred for 1 hr at room temperature. The solution is evaporated in vacuo to a solid. The solid is recrystallized twice from ethyl acetate to give 1.5 g of white crystalline product, mp 191°–192.5° C.

EXAMPLE IV

N-[2α,7α,11bα]-(1,3,4,6,7,11b-Hexahydro-7-phenyl-2H-benzo[a]quinolizin-2-yl)-N,N'-diphenylurea 1.35 g (3.8 mmol) of [2α,7α,11bα]-1,3,4,6,7,11b-hexahydro-N,7-diphenyl-2H-benzo-[a]quinolizin-2-amine (V) is combined with 0.50 g (4.2 mmol) of phenyl isocyanate in 15 ml of dry methylene chloride and stirred for 3 hrs. An additional 0.10 g of phenyl isocyanate is added and the solution is stirred for 16 hrs at room temperature. A white solid product is filtered off. The filtrate is evaporated in vacuo to a residue, which is partially dissolved in 10 ml of methylene chloride. The undissolved white solid is filtered to give a second crop of product. The combined crops are recrystallized twice from methylene chloride/ethanol to give 0.88 g of white solid, mp 207°–208° C.

EXAMPLE V

N-{[2α,7α,11bα]-1,3,4,6,7,11b-Hexahydro-7-phenyl-2H-benzo[a]-2-quinolizinyl}-N-phenylurea 2.98 gms (8.43 m mole) of [2α,7α,11bα]-1,3,4,6,7,11b-hexahydro-N; 7-diphenyl-2H-benzo[a] quinolizine-2-amine is treated with excess phosgene at −20° C. in dry methylene chloride then allowed to stir at room temperature for 0.5 hr. The solvent is removed in vacuo to give an amorphous solid intermediate. The intermediate is redissolved in 50 ml methylene chloride, treated with excess anhydrous ammonia at room temperature and allowed to stir overnight. The reaction mixture is filtered, the filtrate washed 4x (until neutral) with water and the organic phase dried over potassium carbonate. The solvent is removed in vacuo to give an off-white solid which is recrystallized from methylene chloride (minimum)-acetone. The product is recrystallized again to afford the title compound as a white solid, m.p. 181°–183° C.

EXAMPLE VI

N-{[2α,7α,11bα]-1,3,4,6,7,11b-Hexahydro-7-phenyl-2H-benzo[a]-2-quinolizinyl}-N-phenyl-N',N'-dimethylurea Monohydrochloride 2.98 gms (8.43 m mole) of [2α,7α,11bα]-1,3,4,6,7,11b-hexahydro-N, 7-diphenyl-2H-benzo[a] quinolizine-2-amine is treated with excess phosgene at −20° C. in dry methylene chloride then allowed to stir at room temperature for 0.5 hr. The solvent is removed in vacuo to give an amorphous solid intermediate. The intermediate is redissolved in 50 ml of methylene chloride, treated with excess anhydrous dimethylamine at room temperature and allowed to stir overnight. The reaction mixture is filtered, the filtrate washed with a saturated sodium carbonate solution, then with water until neutral and the organic phase dried over potassium carbonate. The solvent is removed in vacuo to give a hard yellow glass. The glass is redissolved in acetone and treated with anhydrous ethereal/HCl solution until acidic. The mixture is evaporated to dryness in vacuo, redissolved in acetone and precipitated with ether. Recrystallization from methylene chloride (minimum)-acetone-ether affords the title compound as a white solid, m.p. 222°–224° C.

EXAMPLE VII

N-{[2α,7α,11bα]-(1,3,4,6,7,11b-Hexahydro-7-phenyl-2H-benzo[a]-quinolizin-2yl}-N-phenyl-N'(1-methylethyl)urea 2.98 gms. (8.43 m moles) of [2α,7α,11bα]-1,3,4,6,7,11b-hexahydro N,7-diphenyl-2H-benzo[a] quinolizin-2-amine is dissolved in toluene and treated with 3.98 gms (47 m moles) of isopropylisocyanate in a pressure bottle and heated on a steam bath for 65 hrs. The crude reaction mixture is treated with Darco G and Norit A charcoal, filtered, and the solvent removed in vacuo to give a solid mass. Recrystallization from acetone affords the title compound as a white solid, m.p. 176°–179° C.

For pharmaceutical purposes, the compounds according to the present invention are administered to warm-blooded animals enterally or parenterally as active ingredients in customary dosage unit compositions, that is, compositions in dosage unit form consisting essentially of an inert pharmaceutical carrier and one effective dosage unit (1-500 mg) of the active ingredient, such as tablets, coated pills, capsules, wafers, powders, solutions, suspensions, emulsions, syrups, suppositories, and the like.

The following examples illustrate a few pharmaceutical dosage unit compositions comprising a compound of the present invention as an active ingredient and represent suitable modes for putting the invention into practical use. The parts are parts by weight unless otherwise specified.

EXAMPLE VIII

Tablets

The tablet composition is compounded from the following ingredients:

| | |
|---|---|
| N—[2α,7α,11bα]-(1,3,4,6,7,11b-hexahydro-7-phenyl-2H-benzo[a]-quinolizin-2-yl)-N'—methyl-N—phenyl-urea perchlorate | 200.0 parts |
| Lactose | 45.0 parts |
| Corn Starch | 45.0 parts |

| | |
|---|---|
| Colloidal Silicic Acid | 2.0 parts |
| Soluble Starch | 5.0 parts |
| Magnesium Stearate | 3.0 parts |
| TOTAL | 300.0 parts |

Preparation

The active ingredient is admixed with part of the excipients, and the mixture is granulated with a solution of the soluble starch in water. After drying of the granulate, the remaining excipients are admixed with it, and the mixture is compressed into 300 mg tablets. Each tablet contains 200 mg of the benzo[a]quinolizine compound and is an oral dosage unit with effective antihypertensive action.

EXAMPLE IX

Coated Pills

The pill core composition is compounded from the following ingredients:

| | |
|---|---|
| N—[2α,7α,11bα]-(1,3,4,6,7,11b-hexahydro-7-phenyl-2H—benzo[a]-quinolizin-2-yl)-N',N'—dimethyl-N—phenyl-urea hydrochloride | 200.0 parts |
| Lactose | 75.0 parts |
| Corn Starch | 65.0 parts |
| Colloidal Silicic Acid | 2.0 parts |
| Soluble Starch | 5.0 parts |
| Magnesium Stearate | 3.0 parts |
| TOTAL | 350.0 parts |

Preparation

The ingredients are compounded as described in Example VIII, and the composition is compressed into 350 mg pill cores which are subsequently coated in a conventional manner with a thin shell consisting essentially of a mixture of sugar, talcum and gum arabic. Each coated pill contains 200 mg of the benzo[a]quinolizine compound and is an oral dosage unit composition with effective anithypertensive action.

EXAMPLE X

Syrup

The syrup composition is compounded from the following ingredients:

| | |
|---|---|
| N—[2α,7α,11bα]-(1,3,4,6,7,11b-hexahydro-7-phenyl-2H—benzo[a]quinolizin-2-yl)-N',N'—dimethyl-N—phenyl-urea hydrochloride | 150.0 parts |
| Cane Sugar | 300.0 parts |
| Glycerol (twice distilled) | 500.0 parts |
| Methyl p-hydroxybenzoate | 3.0 parts |
| Propyl p-hydroxybenzoate | 2.0 parts |
| Flavorings, as desired | |
| Water (distilled) | 4,045.0 parts |
| TOTAL | 5,000.0 parts |

EXAMPLE XI

Tablets

The tablet composition is compounded from the following ingredients:

| | |
|---|---|
| N—[2α,7α,11bα]-(1,3,4,6,7,11b-hexahydro-7-phenyl-2H—benzo[a]quinolizin-2-yl)-N—phenylurea | 250.0 parts |
| Lactose | 20.0 parts |
| Corn Starch | 20.0 parts |
| Colloidal Silicic Acid | 2.0 parts |
| Soluble Starch | 5.0 parts |
| Magnesium Stearate | 3.0 parts |
| TOTAL | 300.0 parts |

Preparation

The active ingredient is admixed with part of the excipients, and the mixture is granulated with a solution of the soluble starch in water. After drying of the granulate, the remaining excipients are admixed with it, and the mixture is compressed into 300 mg tablets. Each tablet contains 250 mg of the benzo[a]quinolizine compound and is an oral dosage unit with effective antihypertensive action.

EXAMPLE XII

Coated Pills

The pill core composition is compounded from the following ingredients:

| | |
|---|---|
| N—[2α,7α,11bα]-(1,3,4,6,7,11b-hexahydro-N—7-phenyl-2H—benzo[a]quinolizin-2-yl)-N—phenylurea | 250.0 parts |
| Lactose | 45.0 parts |
| Corn Starch | 45.0 parts |
| Colloidal Silicic Acid | 2.0 parts |
| Soluble Starch | 5.0 parts |
| Magnesium Stearate | 3.0 parts |
| TOTAL | 350.0 parts |

Preparation

The ingredients are compounded as described in Example, V, and the composition is compressed into 350 mg pill cores which are subsequently coated in a conventional manner with a thin shell consisting essentially of a mixture of sugar, talcum and gum arabic. Each coated pill contains 250 mg of the benzo[a]quinolizine compound and is an oral dosage unit composition with effective antihypertensive action.

We claim:

1. A compound selected from the group consisting of compounds of the formula:

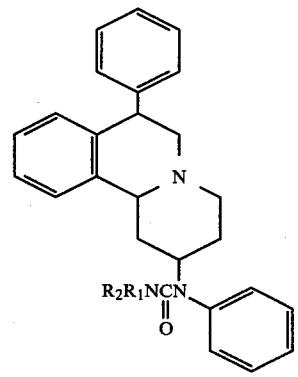

(I)

and non-toxic, pharmaceutically-acceptable acid addition salts thereof, wherein $R_1$ is H or a $C_{1-3}$ lower alkyl and $R_2$ is a $C_{1-6}$ lower alkyl.

2. A compound of claim 1, which is N-[2α,7α,11bα]-(1,3,4,6,7,11b-hexahydro-7-phenyl-2H-benzo[a]quinolizin-2-yl)-N'-methyl-N-phenyl urea (X).

3. A compound of claim 1, which is N-[2α,7α,11bα]-(1,3,4,6,7,11b-hexahydro-7-phenyl-2H-benzo[a]quinolizin-2-yl)-N',N'-dimethyl-N-phenylurea (XV).

4. A compound of claim 1, which is [2α,7β,11bβ]-(1,3,4,6,7,11b-hexahydro-7-phenyl-2H-benzo[a]quinolizin-2-yl)-N'-methyl-N-phenylurea (XI).

5. A compound of claim 1 which is N-[2α,7α,11bα](1,3,4,6,7,11b-hexahydro-7-phenyl-2H-benzo[a]-quinolizin-2-yl]-N-phenyl-N'-(1-methylethyl)urea.

* * * * *